US012766036B2

(12) United States Patent
Rathjen et al.

(10) Patent No.: US 12,766,036 B2
(45) Date of Patent: Oct. 20, 2026

(54) OPHTHALMOLOGICAL LASER TREATMENT DEVICE

(71) Applicant: Ziemer Ophthalmic Systems AG, Port (CH)

(72) Inventors: Christian Rathjen, Bremen (DE); Michael Steinlechner, Zurich (CH)

(73) Assignee: Ziemer Ophthalmic Systems AG, Port (CH)

( * ) Notice: Subject to any disclaimer, the term of this patent is extended or adjusted under 35 U.S.C. 154(b) by 825 days.

(21) Appl. No.: 18/127,157

(22) Filed: Mar. 28, 2023

(65) Prior Publication Data

US 2023/0310213 A1 Oct. 5, 2023

(30) Foreign Application Priority Data

Mar. 29, 2022 (CH) .................................... 353/2022

(51) Int. Cl.
*A61F 9/008* (2006.01)
*A61B 18/20* (2006.01)

(52) U.S. Cl.
CPC .............. *A61F 9/008* (2013.01); *A61B 18/20* (2013.01); *A61F 2009/00897* (2013.01)

(58) Field of Classification Search
CPC ....... A61F 9/008; A61F 9/00802; A61B 18/20
See application file for complete search history.

(56) References Cited

U.S. PATENT DOCUMENTS 9,592,156 B2 3/2017 Huang
9,849,031 B2 * 12/2017 Bischoff ................. A61F 9/008
2002/0198516 A1 * 12/2002 Knopp ............... B23K 26/0096 606/5
2013/0310816 A1 11/2013 Rathjen
2014/0107634 A1 * 4/2014 Vogler ................ A61F 9/00825 606/6
2015/0077705 A1 * 3/2015 Artsyukhovich ...... A61B 3/103 351/206
2016/0089269 A1 * 3/2016 Horvath .............. A61F 9/00825 606/5
2017/0296384 A1 * 10/2017 Fleischmann .......... A61B 90/50
2017/0340483 A1 * 11/2017 Rill ..................... A61F 9/00825
2018/0085257 A1 * 3/2018 Horvath .............. A61F 9/00834
2022/0296418 A1 9/2022 Deutsch et al.

FOREIGN PATENT DOCUMENTS

DE 102019124164 A1 3/2021
EP 3364924 B1 6/2021
WO 2016130207 A1 8/2016

OTHER PUBLICATIONS

Aug. 9, 2022—(CH) Search Report—App 000353/2022.

* cited by examiner

*Primary Examiner* — Thomas E Lazo
(74) *Attorney, Agent, or Firm* — Banner & Witcoff, Ltd.

(57) ABSTRACT

An ophthalmological laser treatment device and methods are disclosed, the ophthalmological laser treatment device comprising: a base station having a treatment laser source, an application head, and an arm configured to provide a beam path for the treatment laser beam; wherein the ophthalmological laser treatment device includes a laser beam monitor, a light signal source, and a control module, the laser beam monitor arranged to receive a light signal generated by the light signal source, the light signal having traveled through the arm along the beam path; wherein the control module is configured to control the ophthalmological laser treatment device using signal characteristics of the light signal.

20 Claims, 5 Drawing Sheets

OPHTHALMOLOGICAL LASER TREATMENT DEVICE

CROSS-REFERENCE TO RELATED APPLICATIONS

The present application claims priority to and the benefit of Switzerland Patent Application 000353/2022 filed Mar. 29, 2022, which is incorporated by reference in its entirety herein.

FIELD OF THE DISCLOSURE

The present disclosure relates to an ophthalmological laser treatment device.

BACKGROUND OF THE DISCLOSURE

Ophthalmological treatment devices which use a laser for eye treatment are known. The ophthalmological treatment device has a laser source which produces a pulsed laser beam. Additionally, the wavelength of the laser light produced by the ophthalmological treatment device is dependent on the type of eye treatment and is typically in the ultraviolet (190 nm to 230 nm) or infrared (780 nm to 1100 nm) range.

The laser beam is typically produced by a laser source arranged in a base station. The laser beam is then guided along a beam path to an application head, where the laser beam is focused onto a patient's eye.

For correct and safe treatment, it is important to ensure that the laser beam is focused onto the correct point, in particular at intended locations on or in the eye. Depending on the specific implementation of the ophthalmological laser treatment device, this can be challenging, in particular if the application head is movable and therefore the beam path is not absolutely static. Additional sources of error include thermal drift and mechanical tolerances.

In particular, where the application head is connected to the base station using an arm, for example a rotatable, telescopic, or articulated arm, and the beam path runs through the arm, movement of joints in the arm can result in changes in the characteristics of the laser beam as it reaches the application head and ultimately the patient's eye.

EP3364924B1 teaches an automatic calibration of a treatment laser using an external grid target which is placed into the beam path at a precisely defined position external to the treatment device, corresponding to the position which a patient's eye will have during treatment. A disadvantage of this method includes the requirement of manually placing the grid target into the beam path.

DE102019124164A1 teaches a laser treatment system and method for characterizing a laser beam whereby the energy and/or position of a pulsed treatment laser beam is intermittently guided onto a sensor.

U.S. Pat. No. 9,592,156B2 discloses a power detector used to monitor the power level of a laser beam in an ophthalmological surgery apparatus.

SUMMARY OF THE DISCLOSURE

It is an object of the disclosure and embodiments disclosed herein to provide an ophthalmological laser treatment device.

In particular, it is an object of the disclosure and embodiments disclosed herein to provide an ophthalmological laser treatment device which does not have at least some of the disadvantages of the prior art.

The present disclosure relates to an ophthalmological laser treatment device. The ophthalmological laser treatment device comprises a base station having a treatment laser source configured to generate a treatment laser beam. The ophthalmological laser treatment device comprises an application head. The ophthalmological laser treatment device comprises an arm arranged between the base station and the application head configured to provide a beam path for the treatment laser beam. The ophthalmological laser treatment device includes a laser beam monitor, a light signal source, and a control module. The laser beam monitor comprises a photodetector array arranged to receive a light signal generated by the light signal source, the light signal having traveled through the arm along the beam path. The control module is configured to receive a photodetector array signal from the photodetector array. The control module is configured to determine, using the photodetector array signal, signal characteristics of the light signal. The control module is configured to control the ophthalmological laser treatment device using the signal characteristics.

In an embodiment, the laser beam monitor is arranged in the base station.

In an embodiment, the light signal source is arranged in the base station and the light signal travels downstream through the arm to the application head and back upstream through the arm to the base station.

In an embodiment, the light signal source is arranged in the application head.

In an embodiment, the laser beam monitor is arranged in the application head. Depending on the implementation, the application head may be part of the arm. In particular, the application head may be integrally formed with the arm.

In an embodiment, the light signal source is arranged in the base station and wherein preferably the light signal travels downstream through the arm to the application head.

In an embodiment, the photodetector array is arranged behind a beam splitter in the beam path. For example, the beam splitter can include a semi-transparent mirror.

In an embodiment, the light signal source includes the treatment laser source, a pilot laser source and/or a light-emitting diode. The light signal source can further include any other light source, e.g., a filament bulb, xenon flash, etc. Depending on an embodiment, two light signal sources are used, in particular the treatment laser source and the pilot laser source.

In an embodiment, the light signal source is a screen configured to display an image generated by the treatment laser source, a pilot laser source and/or a light-emitting diode.

In an embodiment, the arm is a rotatable, telescopic and/or articulated arm comprising one or more internal mirrors arranged in the beam path.

In an embodiment, the control module is configured to determine, using the signal characteristics, a beam position of the treatment laser beam after exiting the arm, a rotational orientation of the treatment laser beam after exiting the arm, a beam power of the treatment laser beam, and/or a laser pulse energy of the treatment laser beam.

In an embodiment, the ophthalmological laser treatment device comprises a scanner, preferably arranged in the base station, configured deflect the treatment laser beam to generate a laser treatment pattern. The control module is configured to control the ophthalmological treatment device, using the signal characteristics, by controlling the scanner. Controlling the scanner may comprise, for example, adjusting the scanner.

In an embodiment, the control module is further configured to generate an alarm message if the signal characteristics do not satisfy one or more pre-defined signal thresholds.

In an embodiment, the control module is configured to control the ophthalmological laser treatment device, using the signal characteristics, by controlling properties of the treatment laser beam, in particular the laser pulse energy of the treatment laser beam and/or the laser beam profile of the treatment laser beam.

In addition to the ophthalmological laser treatment device, the present disclosure also relates to a method for controlling an ophthalmological laser treatment device. The ophthalmological laser treatment device comprises a base station having a treatment laser source configured to generate a treatment laser beam. The ophthalmological laser treatment device comprises an application head, and an arm arranged between the base station and the application head configured to provide a beam path for the treatment laser beam. The ophthalmological laser treatment device includes a laser beam monitor, a light signal source, and a control module. The laser beam monitor comprising a photodetector array arranged to receive a light signal provided by the light signal source, the light signal having traveled through the arm along the beam path. The method comprises receiving, in the control module, a photodetector array signal from the photodetector array. The method comprises determining, in the control module, using the photodetector array signal, signal characteristics of the light signal. The method comprises controlling, in the control module, the ophthalmological laser treatment device using the signal characteristics.

BRIEF DESCRIPTION OF DRAWINGS

The herein described disclosure will be more fully understood from the detailed description given herein below and the accompanying drawings which should not be considered limiting to the disclosure described in the appended claims. The drawings in which:

DESCRIPTION OF THE EMBODIMENTS

Reference will now be made in detail to certain embodiments, examples of which are illustrated in the accompanying drawings, in which some, but not all features are shown. Indeed, embodiments disclosed herein may be embodied in many different forms and should not be construed as limited to the embodiments set forth herein; rather, these embodiments are provided so that this disclosure will satisfy applicable legal requirements. Whenever possible, like reference numbers will be used to refer to like components or parts.

Figure 1:
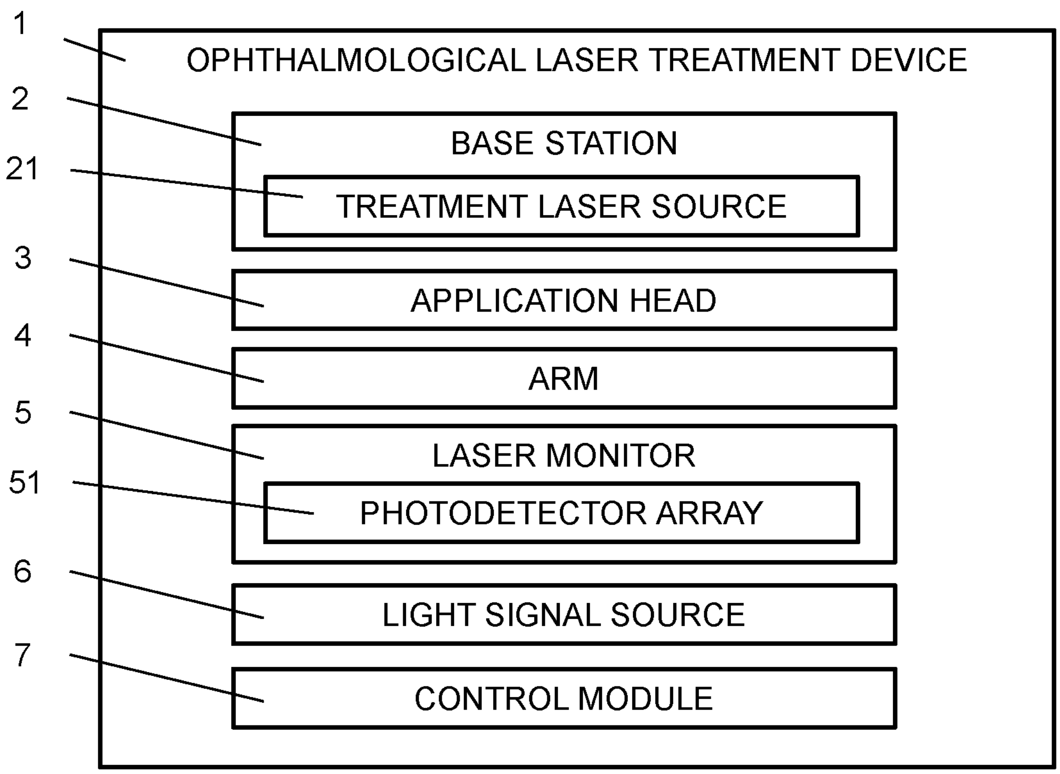
FIG. 1 shows a block diagram illustrating schematically an ophthalmological laser treatment device having a laser beam monitor.

FIG. 1 shows a block diagram illustrating schematically an ophthalmological laser treatment device 1. FIG. 1 and also the remaining block diagrams are figures which schematically illustrate modules and/or elements of various embodiments of the ophthalmological laser treatment device 1 and give an exemplary sequence or arrangement of modules and/or elements, including modules and/or elements in a beam path. Scale and laws of reflection are not depicted or precisely considered.

The ophthalmological laser treatment device 1 comprises a base station 2. The base station 2 is configured as a fixed or mobile apparatus. The ophthalmological laser treatment device 1 has a treatment laser source 21 which generates a treatment laser beam T.

The treatment laser source 21 is configured to, for example, generate an ultraviolet treatment laser beam T having a wavelength of between 190 nm and 230 nm. For example, the treatment laser source 21 comprises an excimer or a solid-state laser which produces such an ultraviolet treatment laser beam T. The excimer laser uses a combination of a noble gas and a reactive gas under high pressure and electrical stimulation. In particular, an excimer laser using argon as the noble gas and fluoride as the reaction gas may be used.

In another example, the treatment laser source 21 is configured to generate an infrared treatment laser beam T having a wavelength of between 780 nm and 1100 nm. For example, the treatment laser source 21 comprises a solid-state laser, such as a frequency converted Nd:YLF laser The treatment laser source 21 will not be described in further detail, however the skilled person is aware that the treatment laser source 21 can comprise, for example, a gain medium, a laser resonator, a laser pump, a pulse generating element, cavity mirrors, coupling mirrors, wavelength tuners, and/or a frequency converter (including one or more non-linear optical crystals).

Depending on the embodiment, the treatment laser beam T is a continuous laser beam or a pulsed laser beam.

In an embodiment, the treatment laser source 21 is configured to generate femtosecond laser pulses, which have pulse widths of typically from 10 fs to 1000 fs (1 fs=$10^{-15}$ s).

Downstream of the treatment laser source 21, the base station 2 includes an optional laser attenuator 22 (not shown) configured to attenuate the treatment laser beam T.

Depending on the embodiment, a beam shaper is included in the base station 2, arranged downstream from the treatment laser source 21. The beam shaper is configured to control the laser beam profile, in particular to redistribute the irradiance and phase of the treatment laser beam T to attain a desired laser beam profile that is maintained along the propagation distance, in particular the propagation distance from the beam shaper to the eye 91.

The ophthalmological laser treatment device 1 further includes, in an embodiment, a shutter arranged in the beam path and configured to stop the treatment laser beam T if an appropriate shutter signal is received. The shutter is implemented, for example, in the base station 2, however it can also be implemented in the arm 4 or in the application head 3.

The base station 2 further includes a scanner system 23 (not shown) which is configured to steer the treatment laser beam T delivered by the treatment laser source 21 onto treatment points on a treatment pattern (comprising a laser trajectory). In an embodiment, the scanner system 23 comprises a divergence modulator for modulating the focal depth, or the treatment height, in the projection direction along a projection axis. The scanner system 23 comprises, for example, a galvanoscanner comprising of one or more controllable mirrors. Alternatively, the scanner system 23 is arranged at least partly in the arm 4 and/or in the application head 3.

In an embodiment, the ophthalmological laser treatment device 1, in particular the base station 2, further includes a beam expander configured to alter a diameter of the treatment laser beam T.

The ophthalmological laser treatment device 1 comprises an application head 3. The application head 3 is designed to guide the treatment laser beam T into or onto the eye 91 of a patient 9 (not shown). The application head 3, for this purpose, can comprise focusing optics 32 (not shown) configured to focus the treatment laser beam T onto one or more treatment points inside or on the eye tissue, in particular the cornea for a pointwise tissue disruption or ablation. The focusing optics comprise a lens system having one or more optical lenses or mirrors. Depending on the embodiment, the focusing optics 32 comprise one or more movable or deformable lenses and/or a drive for moving the entire focusing optics 32 in order to set and adjust the focal depth, or the treatment height, in the projection direction along the projection axis. In a further embodiment, a divergence modulator is provided in the beam path between the treatment laser source 21 and the scanner system 23.

The application head 3 can comprise a patient interface. The application head 3 can be fixed onto the eye 91 by means of the patient interface, for example using suction.

Alternatively, the application head 3 does not have a patient interface for direct contact with the eye 91, but the application head 3 and the eye 91 of the patient 9 are separated by an air gap of several centimeters, for example.

Depending on the embodiment, the application head 3 further comprises an eye tracker configured to track a position and/or orientation of the eye 91 of the patient 9.

The ophthalmological laser treatment device 1 comprises an arm 4 arranged between the base station 2 and the application head 3. The arm 4 is configured to provide a beam path for the treatment laser beam T, such that the treatment laser beam T travels along the inside of the arm 4 from the base station 2 to the application head 3. In an embodiment, the arm 4 comprises one or more joints 41 (not shown) such that the application head 3 is movable and/or rotatable with respect to the base station. Each rotatable joint 41 comprises a mirror arranged in the beam path to reflect the treatment laser beam T along the arm 3.

Because the treatment laser beam T is reflected by each mirror, the treatment pattern generated by the scanner 23 is reflected and/or rotated according to the angles between the beam path and the mirror. Additionally, the treatment laser beam T can shift laterally from its intended position due to imperfectly arranged mirrors, mechanical tolerances at the joints, thermal expansion of the arm 4, the joints 41, or other components of the ophthalmological laser treatment device 1, etc.

In order to monitor the ophthalmological laser treatment device 1, a laser beam monitor 5 is implemented. The laser beam monitor 5 is configured to monitor the treatment laser beam T directly or indirectly. Specifically, the laser beam monitor 5 is configured to monitor the beam path inside the arm 4 along which the treatment laser beam T travels. This involves monitoring signal characteristics of a light signal S which has traveled through the arm 4 along the beam path. The light signal S may travel along the beam path in the same direction as the treatment laser beam T (i.e. a downstream beam path), in a direction opposite to the treatment laser beam T (i.e. an upstream beam path), or in both directions (e.g. downstream then upstream, or upstream followed by downstream). As the light signal S is also affected (e.g. reflected, attenuated, rotated, and/or laterally shifted) by the same mirrors or other optical components arranged in the beam path inside the arm 4, by monitoring the light signal S the ophthalmological laser treatment device 1 is capable of determining how the treatment laser beam T is also affected by the same mirrors or other optical components.

The laser beam monitor 5 is arranged, depending on the embodiment, in the base station 2 or the application head 3, for example. The laser beam monitor 5 comprises a photodetector array 51, for example a one-dimensional, two-dimensional, or three-dimensional array of photodetectors. The photodetector array 51 is implemented, depending on the embodiment, as a CCD sensor or a CMOS sensor, for example.

The photodetector array 51 is configured, depending on the embodiment, to be sensitive to one or more wavelengths (this includes a wavelength band) of light. The wavelengths to which the photodetector array 51 may be sensitive are not limited to visible wavelengths, but are additionally or alternatively also sensitive to light beyond the visible range, for example ultraviolet light and/or infrared light.

Specifically, the photodetector array 51 is configured to generate a photodetector array signal depending on a light signal S received by the photodetector array 51.

In an embodiment, the laser beam monitor 5 further comprises one or more filters arranged in front of the photodetector array 51. The filters are configured to absorb, scatter, convert and/or reflect one or more wavelengths of light. Depending on the embodiment, the filters may further be configured to re-emit energy any absorbed energy in a specific wavelength region.

The filters comprise, for example, one or more colour filters, one or more spectral filters, one or more neutral density filters, one or more bandpass filters, one or more notch filters, one or more edge filters, one or more beam-splitter filters, one or more dichroic filters, one or more colour substrate filters, one or more excitation filters, and/or one or more emission filters. The filters can cover the entire photodetector array 51 or parts thereof, including individual photodetectors (e.g., a Bayer colour filter).

The laser beam monitor 5 further comprises, in an embodiment, optical elements such as mirrors and/or lenses to focus and/or distribute the light signal across the photodetector array 51. For example, the optical elements include microlenses arranged in front of the photodetector array 51 to increase the light signal detected at each photodetector.

The ophthalmological laser treatment device 1 comprises a light signal source 6 configured to generate the light signal S detected by the laser beam monitor 5. Depending on the embodiment, the light signal source 6 is arranged, for example, in the base station 2 or the application head 3.

The ophthalmological laser treatment device 1, in particular using a control module 7 described below, determines the treatment laser beam T characteristics depending on the characteristics of the monitored light signal S. This is possible because the properties of both the pilot laser source as well as the treatment laser source 21 are known, as well as the known properties of the mirrors and/or other optical components arranged in the arm 4.

Additionally, or alternatively, the control module 7 is configured to monitor the scanner system 23 using the characteristics of the monitored light signal S, in particular a position and/or orientation of the light signal S. Monitoring the scanner system 23 comprises, for example, calibrating the scanner system 23 and/or testing the scanner system 23.

In an embodiment, the light signal source 6 includes the treatment laser source 21 and the light signal S includes the treatment laser beam T or part thereof. In particular, the light signal S is generated by a beam splitter arranged in the beam path of the treatment laser beam T such that a part of the treatment laser beam T is split off and diverted onto the laser beam monitor 5. The beam splitter also, in an embodiment, acts as a filter for filtering out particular wavelengths. In this manner, the treatment laser beam T is monitored, by the laser beam monitor 5, directly. In addition to a beam position and a beam rotation, it is possible in this embodiment for the laser beam monitor 5 to directly monitor the treatment laser beam T itself, in particular in order to determine a beam power of the treatment laser beam T and/or a laser pulse energy of the treatment laser beam.

In an embodiment, the light signal source 6 includes a pilot laser source. The pilot laser source is a separate laser source to the treatment laser source 21. The pilot laser source has known characteristics (e.g., wavelength, pulse length) which are, depending on the embodiment, different than the treatment laser source 21.

In an embodiment, the light signal source 6 includes a light-emitting diode. The light-emitting diode (LED) can be implemented as a single LED or an array of LEDs. The one or more LEDs can be configured to produce one or more wavelengths of light.

In an embodiment, the light signal source 6 is a passive source, in particular a screen designed to display light reflected from one or more active sources as described herein. The screen, which is for example, a matt surface having an optional oriented pattern marked on it, acts as an imaging area onto which an image is projected. Specifically, the screen has projected onto it the treatment laser beam T or part thereof. Thereby, the treatment laser beam T indirectly generates the light signal S by illuminating the light signal source 6. Additionally, or alternatively, the screen has fluorescent properties and generates a fluorescent light signal S from the treatment laser beam T. Depending on the embodiment, the active sources which illuminate the (passive) light signal source 6 mentioned above include a pilot laser source and/or one or more LEDs.

In an embodiment, a reflector, in particular a retroreflector, is used as the passive source instead of the screen.

The ophthalmological laser treatment device 1 comprises a control module 7 configured to control the ophthalmological laser treatment device 1. The control module 7 is preferably arranged in the base station 2. The control module 7 embodies a programmable device and comprises, for example, one or more processors, and one or more memory modules (comprising volatile and/or non-volatile memory, e.g., random-access memory and/or flash memory) having stored thereon program code, data, as well as programmed software modules for controlling the processors, and/or other programmable circuits or logic units included in the control module 7, such as ASICs (Application-Specific Integrated Circuits), GPUs (graphics processing units), and/or TPUs (tensor processing units). The memory modules comprise volatile and/or non-volatile storage media, for example random access memory and/or flash memory, respectively. The control module 7 is connected to other components and modules of the ophthalmological laser treatment device 1 as disclosed herein, in particular the treatment laser source 21, the optional laser attenuator 22, the scanner 23, the laser beam monitor 5, and the light signal source 6. The connection is a wired and/or wireless connection configured to exchange control and/or measurement signals.

The control module 7 can further comprise a communication interface. The communication interface is configured for data communication with one or more external devices. Preferably, the communication interface comprises a network communications interface, for example an Ethernet interface, a WLAN interface, and/or a wireless radio network interface for wireless and/or wired data communication using one or more networks, comprising, for example, a local network such as a LAN (local area network), and/or the Internet.

The control module 7 performs one or more steps and/or functions as described herein, for example according to the program code stored in the one or more memory modules. Additionally, or alternatively, the program code can be wholly or partially stored in one or more auxiliary processing devices, for example a computer. The skilled person is aware that at least some of the steps and/or functions described herein as being performed on the processor of the ophthalmological laser treatment device 1 may be performed on one or more auxiliary processing devices connected to the ophthalmological laser treatment device 1 using the communication interface. The auxiliary processing devices can be co-located with the ophthalmological laser treatment device 1 or located remotely, for example on a remote server computer.

The skilled person is also aware that least some of the data associated with the program code (application data) or data associated with a particular patient (patient data) and described as being stored in the memory of the ophthalmological laser treatment device 1 may be stored on one or more auxiliary storage devices connected to the ophthalmological laser treatment device 1 using the communication interface.

The control module 7 stores, in the one or more memory modules, a treatment model. The treatment model is designed for treating the eye 91 of a patient 9 (not shown) using the ophthalmological laser treatment device 1. In particular, the treatment model defines a number of treatment points or treatment curves onto which the treatment laser beam T is directed.

In an embodiment, the control module 7 further stores, in the one or more memory modules, test data and/or calibration data. The test data and/or calibration data is generated during a test routine and/or a calibration routine, respectively. To this end, the one or more memory modules further comprise, for example, program code configured such that the control module 7 performs the test routine and/or the calibration routine, respectively. The test routine and/or the calibration routine are performed, for example, prior to treatment, such that it is ensured that the ophthalmological treatment device 1 is performing according to specification, in particular that the signal characteristics satisfy one or more pre-defined signal thresholds. The test routine and/or the maintenance routine involve one or more of the components of the ophthalmological laser treatment device 1, for example the treatment laser source 21, the light signal source, and/or the scanner system 23. In an embodiment where the ophthalmological laser treatment device 1 comprises a shutter, the test routine and/or calibration routine can also be performed with the patient 9 in position under the application head 91.

The ophthalmological laser treatment device 1 optionally includes a user interface comprising, for example, one or more user input devices, such as a keyboard, and one or more output devices, such as a display 8. The user interface is configured to receive user inputs from an eye treatment professional, in particular based on, or in response to, information displayed to the eye treatment professional using the one or more output devices.

Figure 2:
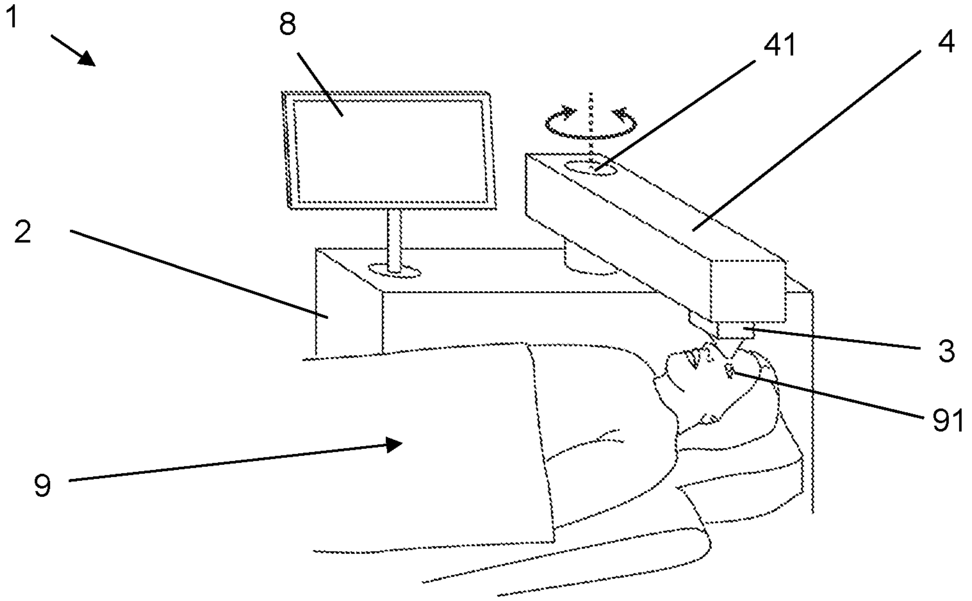
FIG. 2 shows a perspective view of an ophthalmological laser treatment device with a horizontally rotatable arm.
Figure 3:
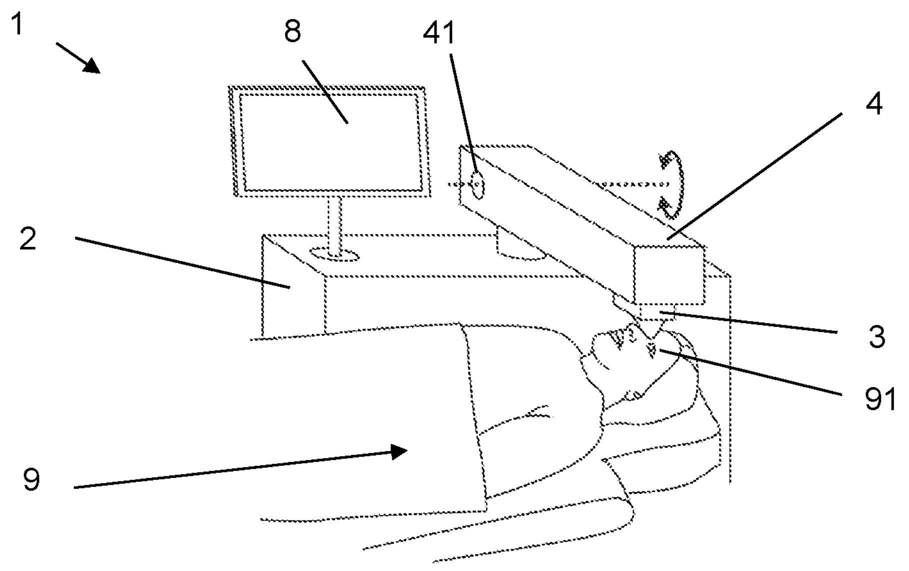
FIG. 3 shows a perspective view of an ophthalmological laser treatment device with a vertically rotatable arm.
Figure 4:
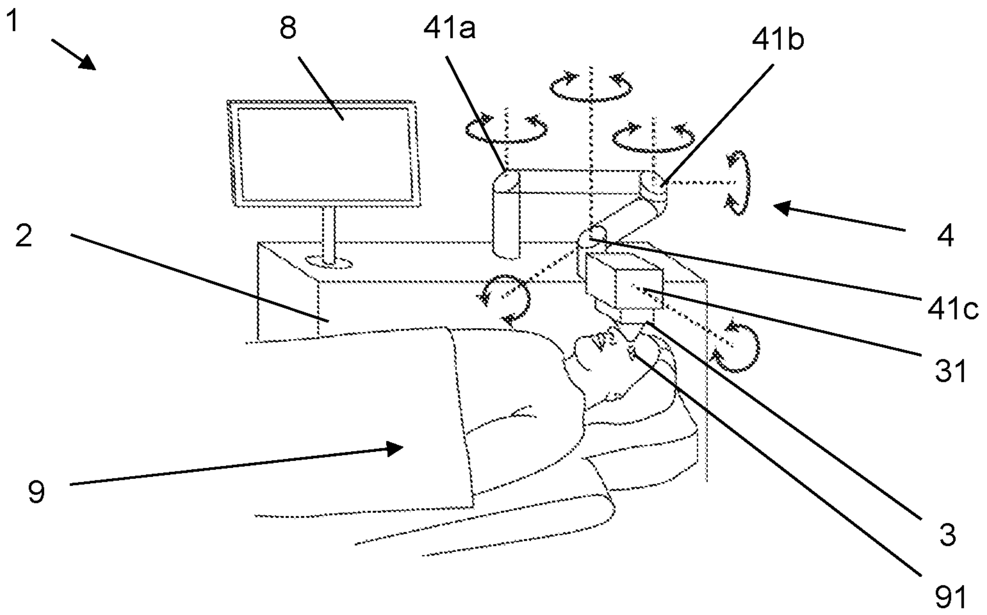
FIG. 4 shows a perspective view of an ophthalmological laser treatment device with an articulated arm.

FIGS. 2 to 4 show three different embodiments of the ophthalmological laser treatment device 1, each having a different embodiment of the arm 4. Other embodiments are possible, and depending on the configuration of the base station 2, in particular whether the base station 2 is itself height-adjustable or not, certain aspects of at least some of the three embodiments described below can be modified. Specifically, certain joints 41 for adjusting a vertical height of the application head 3 are superfluous and may be omitted.

In FIG. 2, the arm is rotatable about the joint 41, such that the arm 4 can swing horizontally over a reclining patient 9 such that the application head 3 is moved into position above the eye 91 of the patient 9.

In FIG. 3, the arm 4 is rotatable about the joint 41 such that the arm 4 can swing vertically over a reclining patient 9 such that the application head 3 is moved into position above the eye 91 of the patient 9.

In FIG. 4, the arm 4 is an articulated arm 4 rotatable about the joints 41*a*, 41*b*, 41*c* such that the application head 3 can be flexibly moved into position above the eye 91 of the patient 9. Each joint 41*a*, 41*b*, 41*c* enables one or more rotations, for example the joint 41*b* allows both a rotation in the vertical as well as the horizontal plane. Additionally, it can be seen that the application head 3 has a joint 31 about which the application head 3 can be rotated.

FIGS. 5 to 8 show schematic block diagrams of different embodiments of the ophthalmological laser treatment device 1, in particular showing the laser beam monitor 5 and the light signal source 6 arranged in different places. These FIGS. 5 to 8 all show the ophthalmological laser treatment device 1 as having an articulated arm 4, however this is for purposes of illustration only and is not intended to be limiting. Specifically, the particular arrangements of the laser beam monitor 5 and the light signal source 6 as shown are transferable to other embodiments of the present disclosure in which the arm 4 is fixed, rotatable, and/or telescopic, for example.

Figure 5:
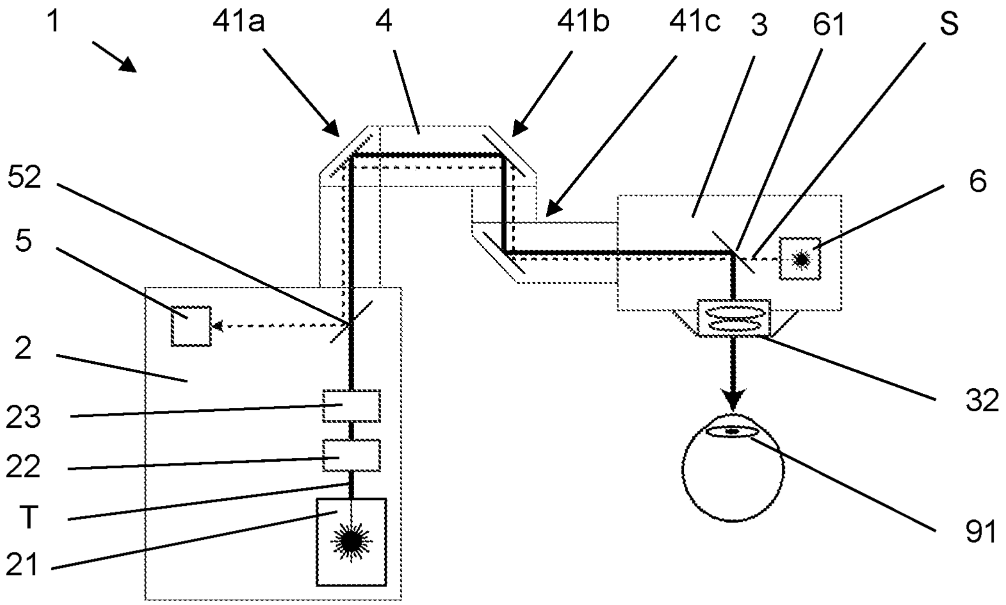
FIG. 5 shows a block diagram illustrating schematically an ophthalmological laser treatment device having a laser beam monitor arranged in the base station.

In FIG. 5, the light signal source 6 is arranged in the application head 3 and the laser beam monitor 5 is arranged in the base station 2. The light signal source 6 is arranged behind a beam splitter 61 which is configured to reflect the treatment laser beam T towards the optical elements 32 in the application head 3 while also allowing from transmission of the light signal S into the beam path. Thereby, the light signal S travels through the arm 4 along the beam path upstream, i.e., in the direction opposite to the direction of the treatment laser beam T. The light signal S enters the base station 2 and again meets a beam splitter 52 arranged in the beam path and configured to reflect the light signal S towards the laser beam monitor 5. The beam splitter 52 is configured to allow for the transmission of the treatment laser beam T, or a substantial proportion thereof. In such a manner, the laser beam monitor 5 is able to monitor any changes in the beam path, in particular due to a rotation at the joints 41*a*, 41*b*, 41*c* and/or a thermal expansion or contraction which would change the properties of the treatment laser beam T.

Figure 6:
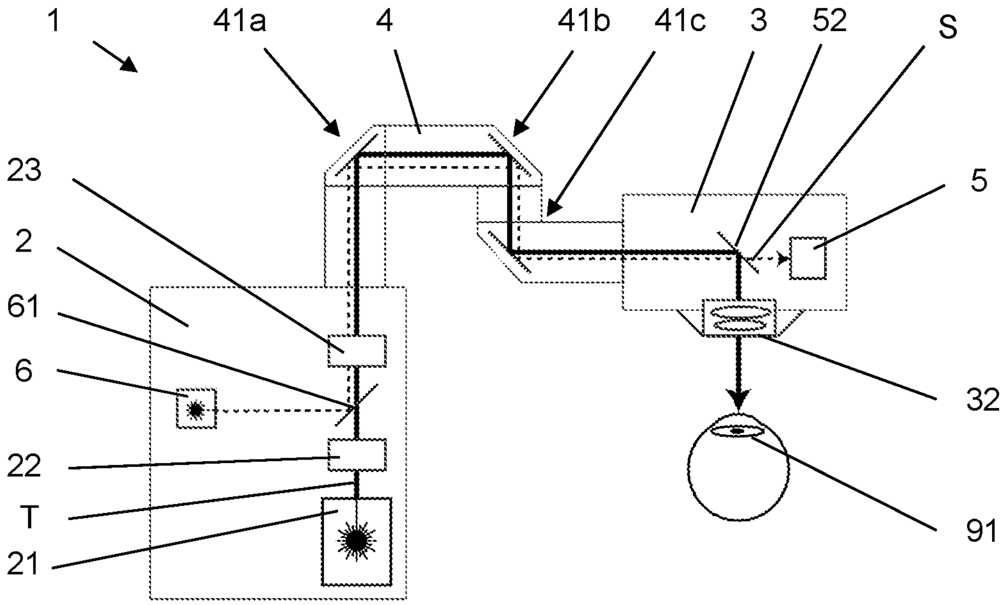
FIG. 6 shows a block diagram illustrating schematically an ophthalmological laser treatment device having a laser beam monitor arranged in the application head.
Figure 7:
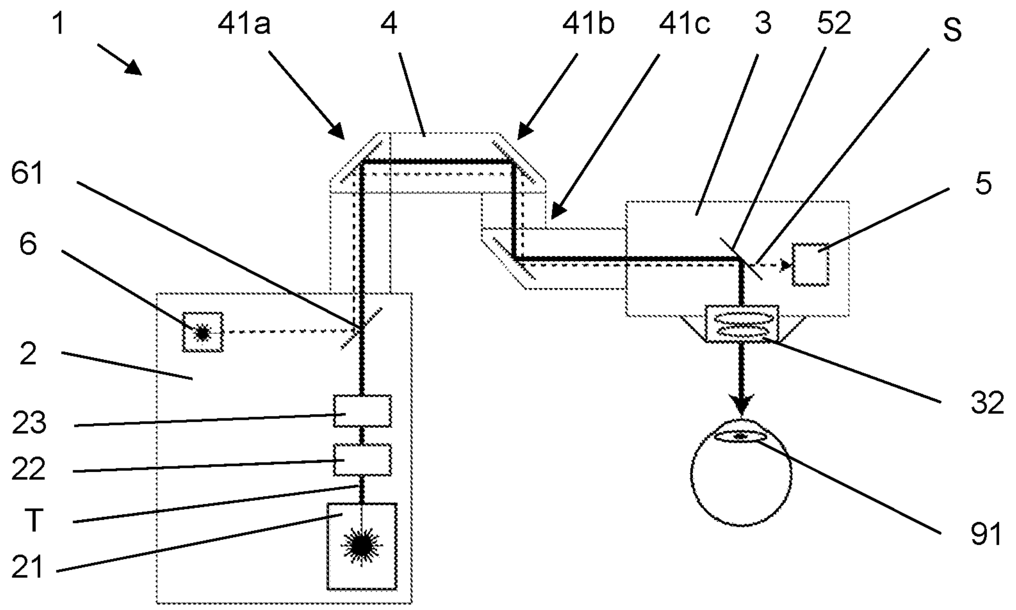
FIG. 7 shows a block diagram illustrating schematically an ophthalmological laser treatment device having a laser beam monitor arranged in the application head.

In FIGS. 6 and 7, the light signal source 6 is arranged in the base station 2 and the laser beam monitor 5 is arranged in the application head 3. As described above with reference to FIG. 6, there are two beam splitters 61, 52 arranged in the beam path of the treatment laser beam T which are configured to couple the light signal S into and out of the beam path of the treatment laser beam T, respectively. The beam splitters are arranged in the base station 2 and the application head 3, respectively. As above, the laser beam monitor 5 is able to monitor any changes in the beam path, in particular due to a rotation at the joints 41*a*, 41*b*, 41*c*, a thermal expansion or contraction, and/or movement play due to mechanical tolerances, which would change the properties of the treatment laser beam T.

FIGS. 6 and 7 differ in that in FIG. 6, the beam splitter 61 which couples the light signal S into the beam path is arranged in between the attenuator 22 and the scanner 23, while in FIG. 7, the beam splitter 61 is arranged downstream from the scanner 23. By arranging the beam splitter 61 upstream from the scanner, as is shown in FIG. 6, the treatment pattern generated by the scanner 23 is applied not only to the treatment laser beam T but also to the light signal S. Thereby, a rotation of the light signal S, due to rotation of the joints 41*a*, 41*b*, 41*c*, for example, is easily detected by the laser beam monitor 5.

In an embodiment, the treatment laser source 21 provides the light signal S monitored by the laser beam monitor 5. In other words, the treatment laser beam T is also the light signal S. Thereby, a separate light signal source 6 is not required. Further, the beam splitter 61 shown is not required. According to this embodiment, not only can any changes in the beam path be monitored, but also the properties of the treatment laser beam T are monitored, in particular the beam power, a laser pulse energy, and/or a laser beam profile of the treatment laser beam T.

In an embodiment, the light signal source 6 comprises both the treatment laser source 21 and the pilot laser source. In this embodiment, the treatment laser source 21 and the pilot laser source are arranged, for example, in the base station 2, the beam splitter 61 being arranged downstream of the treatment laser source 21 and configured to couple the pilot laser source into the beam path, in particular upstream of the scanner system 23. The laser beam monitor 5 is preferably arranged in the application head 5 behind the beam splitter 52.

Depending on the implementation, the treatment laser source 21 and the pilot laser source are configured to be active simultaneously or during different and/or overlapping time periods. Further, the pilot laser source and the treatment laser source 21 are configured to have either the same beam diameter or a different beam diameter.

For example, the pilot laser source can be configured to produce the light signal S to have a smaller diameter than the diameter of the treatment laser beam T. In such an example, the light signal S produced by the pilot laser source and detected by the laser beam monitor 5 is used to determine a rotational orientation of the treatment model. The treatment laser beam T, on the other hand, is only monitored when in the zero position (i.e., the scanner system 23 does not steer the treatment laser beam T off a center axis of the beam path). The properties of the treatment laser beam T being monitored include, for example, the beam power and/or a laser pulse energy of the treatment laser beam T.

Figure 8:
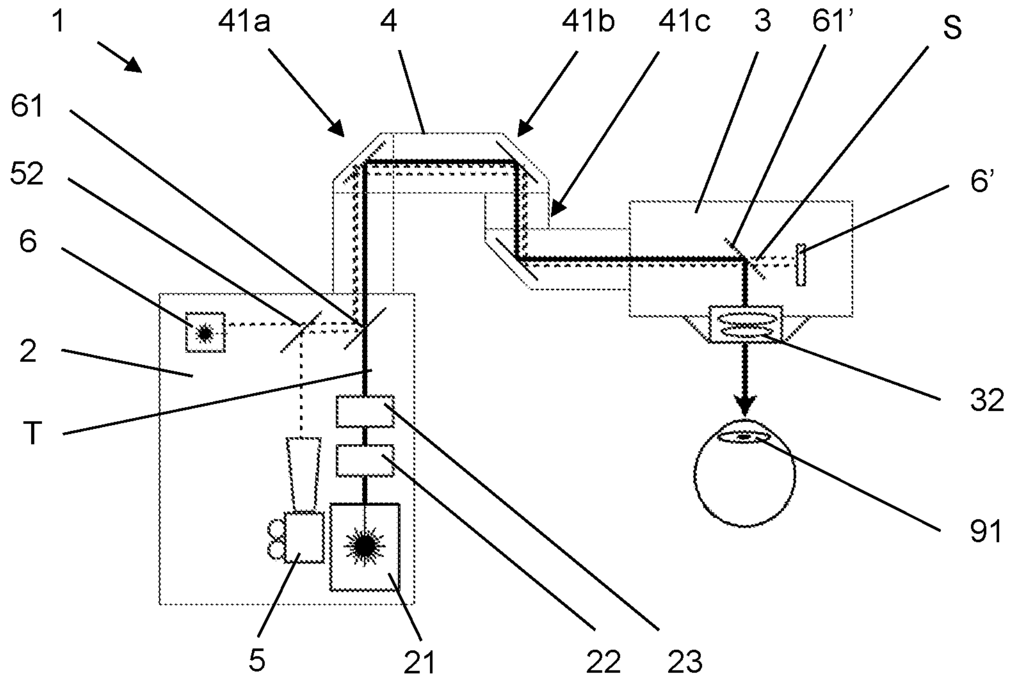
FIG. 8 shows a block diagram illustrating schematically an ophthalmological laser treatment device having a laser beam monitor arranged in the base station.

In FIG. 8, the laser beam monitor 5 is arranged in the base station 2 and the light signal source 6' is arranged in the application head 3. The light signal source 6' is implemented as a screen, for example a matt surface having an optional oriented pattern marked on it, which displays light from a primary signal source 6 as shown, or alternatively is the treatment laser source 21 itself. The light signal source 6' is arranged behind a beam splitter, similarly to the embodiment shown in FIG. 5. The light signal S travels upstream, relative to the treatment laser beam T, from the application head 3 to the base station 2. A beam splitter 52 is arranged to redirect the light signal S to the laser beam monitor 5.

In an embodiment, the light signal source 6' is implemented as a retroreflector.

Figure 9:
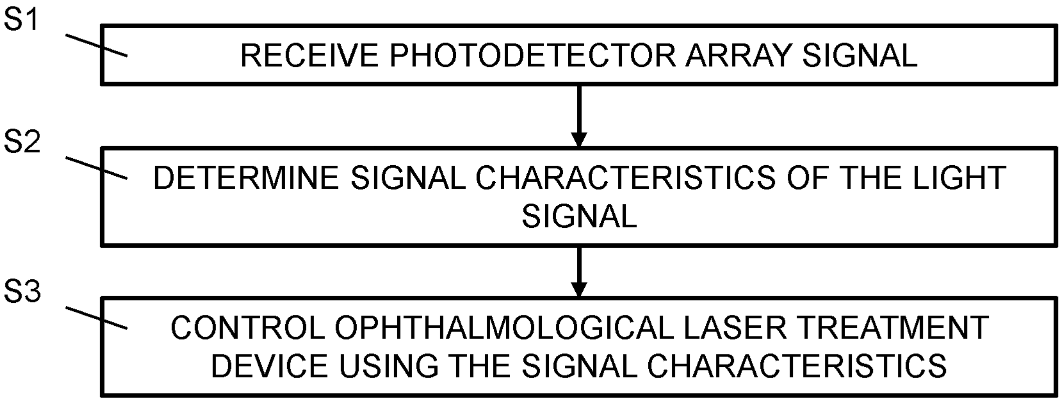
FIG. 9 shows a flow diagram illustrating a number of steps for beam monitoring of an ophthalmological laser treatment device.

FIG. 9 shows a flow diagram illustrating a number of steps for monitoring the ophthalmological laser treatment device 1.

In a step S1, the control module 7 is configured to receive, from the laser beam monitor 5, in particular from the photodetector array 51, a photodetector array signal.

In a step S2, the control module 7 is configured to determine, using the photodetector array signal, signal characteristics of the light signal S.

In a step S3, the control module 7 is configured to control the ophthalmological laser treatment device 1 using the signal characteristics.

In an embodiment, the control module 7 is configured to control the ophthalmological laser treatment device 1 by controlling the scanner 23 using the signal characteristics. For example, the control module 7 is configured to transmit, to the scanner, a control adjustment signal configured to control the scanner to laterally shift and/or rotate the treatment model, according to the signal characteristics. Thereby, the planned treatment of the eye 91 of the patient 9 is unaffected by changes in the arm 4, for example due to thermal expansion or mechanical tolerances in the joints 41, because the ophthalmological laser treatment device 1 adjusts the treatment laser beam T to compensate for any such changes.

In an embodiment, the control module 7 is configured to control the ophthalmological laser treatment device 1 by controlling the treatment laser source 21 using the signal characteristics.

In an embodiment, the control module 7 is configured to control the ophthalmological laser treatment device 1 by controlling the attenuator 22.

In an embodiment, the control is configured to control the ophthalmological laser treatment device 1 by controlling the shutter.

In an embodiment, the control module 7 is configured to determine, using the signal characteristics, properties of the treatment laser beam T and is configured to control the treatment laser source 21 by determining these properties and adjusting the treatment laser source 21 accordingly. The properties include a beam position of the treatment laser beam T after exiting the arm, a rotational orientation of the treatment laser beam T after exiting the arm, a beam power of the treatment laser beam T, a laser pulse energy of the treatment laser beam T, and/or a laser beam profile of the treatment laser beam T. The properties of the treatment laser beam T can further include, for example, a beam dispersion, a beam central wavelength, and/or a beam wavelength distribution. The control module 7 is configured to control the ophthalmological laser treatment device 1 using one or more of the properties of the treatment laser beam T. For example, the control module 7 is configured to control the ophthalmological laser treatment device 1 such that the aforementioned properties satisfy one or more pre-defined conditions, e.g., have a particular set-point value or lie within a particular range around the set-point value.

In an embodiment, the control module 7 is further configured to generate an alarm message if the signal characteristics do not satisfy one or more pre-defined signal thresholds (e.g. the signal characteristics are above or below a maximum or minimum signal threshold, respectively, or the signal characteristics are not within a range indicated by an upper and a lower signal threshold). The signal thresholds define, for example, a maximum value and/or a minimum value of the beam power and/or of the laser pulse power. The alarm message can be, for example, prominently displayed on the display 8 of the ophthalmological laser treatment device 1. The ophthalmological laser treatment device 1 can also be configured to engage the shutter to stop the treatment laser beam T and/or power down the treatment laser source 21.

The above-described embodiments of the disclosure are exemplary and the person skilled in the art knows that at least some of the components and/or steps described in the embodiments above may be rearranged, omitted, or introduced into other embodiments without deviating from the scope of the present disclosure.

The invention claimed is:

1. An ophthalmological laser treatment device comprising:

a base station having a treatment laser source configured to generate a treatment laser beam;

an application head; and an arm arranged between the base station and the application head configured to provide a beam path for the treatment laser beam, wherein the ophthalmological laser treatment device includes a laser beam monitor, a light signal source, and a control module, the laser beam monitor comprising a photodetector array arranged to receive a light signal generated by the light signal source, the light signal having traveled through the arm along the beam path, wherein the control module is configured to:

receive a photodetector array signal from the photodetector array, determine, using the photodetector array signal, signal characteristics of the light signal, and control the ophthalmological laser treatment device using the signal characteristics, wherein the control module is configured to determine, using the signal characteristics, at least one of the following properties of the treatment laser beam: a rotational orientation of the treatment laser beam after exiting the arm, a beam power of the treatment laser beam, a laser pulse energy of the treatment laser beam, or a laser beam profile of the treatment laser beam.

2. The ophthalmological laser treatment device of claim 1, wherein the laser beam monitor is arranged in the base station.

3. The ophthalmological laser treatment device of claim 2, wherein the light signal source is arranged in the base station and the light signal travels downstream through the arm to the application head and back upstream through the arm to the base station.

4. The ophthalmological laser treatment device of claim 2, wherein the light signal source is arranged in the application head.

5. The ophthalmological laser treatment device of claim 1, wherein the laser beam monitor is arranged in the application head.

6. The ophthalmological laser treatment device of claim 5, wherein the light signal source is arranged in the base station.

7. The ophthalmological laser treatment device of claim 1, wherein the photodetector array is arranged behind a beam splitter in the beam path.

8. The ophthalmological laser treatment device of claim 1, wherein the light signal source includes at least one of: the treatment laser source, a pilot laser source, or a light-emitting diode.

9. The ophthalmological laser treatment device of claim 1, wherein the light signal source is a screen configured to display an image generated by at least one of: the treatment laser source, a pilot laser source, or a light-emitting diode.

10. The ophthalmological laser treatment device of claim 1, wherein the arm is an articulated arm comprising one or more internal mirrors arranged in the beam path.

11. The ophthalmological laser treatment device of claim 1, wherein the control module is configured to determine, using the signal characteristics, at least one of the following properties of the treatment laser beam: a beam position of the treatment laser beam after exiting the arm, a rotational orientation of the treatment laser beam after exiting the arm, a beam power of the treatment laser beam, a laser pulse energy of the treatment laser beam, or a laser beam profile of the treatment laser beam.

12. The ophthalmological laser treatment device of claim 1, wherein the ophthalmological laser treatment device comprises a scanner configured to deflect the treatment laser beam to generate a laser treatment pattern, and wherein the control module is configured to control the ophthalmological treatment device, using the signal characteristics, by controlling the scanner.

13. The ophthalmological laser treatment device of claim 1, wherein the control module is further configured to generate an alarm message if the signal characteristics do not satisfy at least one pre-defined signal threshold.

14. The ophthalmological laser treatment device of claim 1, wherein the control module is configured to control the ophthalmological laser treatment device, using the signal characteristics, by controlling the properties of the treatment laser beam, wherein the properties of the treatment laser beam include at least one of the following: the laser pulse energy of the treatment laser beam or the beam profile of the treatment laser beam.

15. A method for controlling an ophthalmological laser treatment device, the ophthalmological laser treatment device comprising:

a base station having a treatment laser source configured to generate a treatment laser beam, an application head, and an arm arranged between the base station and the application head configured to provide a beam path for the treatment laser beam;

wherein the ophthalmological laser treatment device includes a laser beam monitor, a light signal source, and a control module, the laser beam monitor comprising a photodetector array arranged to receive a light signal provided by the light signal source, the light signal having traveled through the arm along the beam path, the method comprising:

receiving, in the control module, a photodetector array signal from the photodetector array;

determining, in the control module, using the photodetector array signal, signal characteristics of the light signal; and controlling, in the control module, the ophthalmological laser treatment device using the signal characteristics, wherein determining, in the control module, the signal characteristics, comprises determining at least one of the following properties of the treatment laser beam: a rotational orientation of the treatment laser beam after exiting the arm, a beam power of the treatment laser beam, a laser pulse energy of the treatment laser beam, or a laser beam profile of the treatment laser beam.

16. An ophthalmological laser treatment device comprising:

a base station having a treatment laser source configured to generate a treatment laser beam;

an application head;

an arm arranged between the base station and the application head configured to provide a beam path for the treatment laser beam;

a light signal source configured to generate a light signal;

a laser beam monitor comprising a photodetector array configured to receive the light signal generated by the light signal source, the light signal having traveled through the arm along the beam path; and a control module configured to:

receive a photodetector array signal from the laser beam monitor, determine, using the photodetector array signal, signal characteristics of the light signal, and control the ophthalmological laser treatment device using the determined signal characteristics, wherein the control module is configured to determine, using the signal characteristics, at least one of the following properties of the treatment laser beam: a rotational orientation of the treatment laser beam after exiting the arm, a beam power of the treatment laser beam, a laser pulse energy of the treatment laser beam, or a laser beam profile of the treatment laser beam.

17. The ophthalmological laser treatment device of claim 16, wherein the light signal travels downstream through the arm to the application head and back upstream through the arm to the base station.

18. The ophthalmological laser treatment device of claim 16, wherein the light signal source includes at least one of: the treatment laser source, a pilot laser source, or a light-emitting diode.

19. The ophthalmological laser treatment device of claim 16, wherein the control module is configured to determine, using the signal characteristics, at least one of the following properties of the treatment laser beam: a beam position of the treatment laser beam after exiting the arm, a rotational orientation of the treatment laser beam after exiting the arm, a beam power of the treatment laser beam, a laser pulse energy of the treatment laser beam, or a laser beam profile of the treatment laser beam.

20. The ophthalmological laser treatment device of claim 16, wherein the ophthalmological laser treatment device comprises a scanner configured to deflect the treatment laser beam to generate a laser treatment pattern, and wherein the control module is configured to control the ophthalmological treatment device, using the signal characteristics, by controlling the scanner.

* * * * *